United States Patent [19]
Apffel, Jr. et al.

[11] Patent Number: 5,495,108
[45] Date of Patent: Feb. 27, 1996

[54] ORTHOGONAL ION SAMPLING FOR ELECTROSPRAY LC/MS

[75] Inventors: James A. Apffel, Jr., Palo Alto; Mark H. Werlich, Fremont; James L. Bertsch, Palo Alto, all of Calif.

[73] Assignee: Hewlett-Packard Company, Palo Alto, Calif.

[21] Appl. No.: 273,250

[22] Filed: Jul. 11, 1994

[51] Int. Cl.$^6$ .............................. B01D 59/46; H01J 49/00
[52] U.S. Cl. ............................................................ 250/288
[58] Field of Search ................................. 250/288, 288 A

[56] References Cited

U.S. PATENT DOCUMENTS

| | | |
|---|---|---|
| Re. 34,757 | 10/1994 | Smith ........................... 250/288 |
| 4,667,100 | 5/1987 | Lagna ........................... 250/288 A |
| 5,171,990 | 12/1992 | Mylchreest ...................... 250/288 |
| 5,285,064 | 2/1994 | Willoughby ...................... 250/288 |

Primary Examiner—Constantine Hannaher
Assistant Examiner—Virgil O. Tyler

[57] ABSTRACT

The invention teaches the uses of a plurality of electric fields and of orthogonal spray configurations of vaporized analyte which combine so as to operate to enhance the efficiency of analyte detection and mass analysis with a mass spectrometer by reducing vapor in the vacuum system and concomitant noise. Several embodiments of the invention are described for purposes of illustration.

19 Claims, 4 Drawing Sheets

ORTHOGONAL ION SAMPLING FOR ELECTROSPRAY LC/MS

INTRODUCTION

The invention relates to a method and apparatus for obtaining improved ion collection efficiency in electrospray on LC/MS.

Initial systems for electrospray LC/MS utilized flow splitters that divided the HPLC column effluent in such a way that a small portion, typically 5–50 micro liters per minute, was introduced into the "spray chamber" while the major portion was directed to a waste or fraction collector. Because low flow rates were introduced into electrospray systems, it became possible to generate spray solely through the use of electrostatic forces. Since ES/MS is a concentration sensitive detector, this does not result in loss of sensitivity when compared with introduction of all the flow into the spray chamber (assuming equal charging and sampling efficiencies). However, the use of flow splitters has gained a bad reputation due to potential plugging problems and poor reproducibility.

Newer electrospray systems generate a charged spray through the combination of electrostatic forces and an assisted nebulization. The assisted nebulization generates an aerosol from the HPLC effluent, while the electric field induces a charge on the droplets, which ultimately results in the generation of desolvated analyte ions via an ion evaporation process. The assisted nebulization can be done with pneumatic, ultrasonic, or thermal nebulization or by some other nebulization technique.

In each of these newer assisted nebulizer systems, it has been necessary to design the system so that the solvated droplets present in the aerosol do not enter the vacuum system. This has been accomplished in several ways.

In one currently available system, the aerosol is sprayed "off axis" at an angle of as much as 45 degrees with respect to the axis of the sampling orifice. In addition, a counter current drying gas is sprayed around the sampling orifice to blow the solvated droplets away from the orifice. The gas pressures typically used generates a plume of small droplets and optimal performance appears to be limited to a flow rate of 200 microliters per minute or lower.

In another currently available system, an aerosol is generated pneumatically and aimed directly at the entrance of a heated capillary tube into the vacuum system. Instead of desolvated ions entering the capillary, large charged droplets are drawn into the capillary and the droplets are desolvated while in transit. The evaporation process takes place in the capillary as well. A supersonic jet of vapor exits the capillary and the analyte ions are subsequently focused, mass analyzed and detected. There are several disadvantages to this system. The use of the high temperature capillary may result in thermal degradation of thermally labile samples. In the supersonic jet expansion, the desolvated ions and vapor may recondense resulting in solvent clusters and background signals. While these clusters may be re-dissociated by collisionally induced processes, this may interfere in identification of structural characteristics of the analyte samples which are intentionally subjected to collisionally induced dissociation. The large amount of solvent vapor, ions and droplets exiting the capillary require that the detector be arranged substantially off axis with respect to the capillary to avoid noise due to neutral droplets striking the detector. The additional solvent entering the vacuum requires larger pumps.

In another currently available system, the spray is generated ultrasonically. The system is used in conjunction with a counter current drying gas and is usually operated with the spray directed at the sampling capillary. The main disadvantages of this system, from the practitioner's point of view, are that optimal performance is effectively limited to less than 500 microliters per minute and that there are serious problems with aqueous mobile phases. Furthermore, the apparatus is complex and prone to mechanical and electronic failures.

In another commonly used system, a pneumatic nebulizer is used at substantially higher inlet pressures (as compared with other systems). This results in a highly collimated and directed droplet beam. This is aimed off-axis to the side of the orifice in the nozzle cap. Although this works competitively, there is still some noise which is probably due to stray droplets. The nebulizer jet has to be aimed carefully to minimize noise while maintaining signal intensity.

SUMMARY OF INVENTION

The invention provides the capability of conducting atmospheric pressure ionization, API, whether electrospray or atmospheric pressure chemical ionization (APCI), with conventional High Performance Liquid Chromatography at flow rates of greater than 1 ml/minute without flow splitting. The invention allows desolvated ions to be separated from comparatively large volumes of vaporized column effluent, and then, while keeping out as much of the solvent as possible, introducing the desolvated ions into the vacuum system for mass detection and analysis while introducing as little of the solvent as possible. The invention provides the capability of separating desolvated ions of interest from the large volumes of vapor, and directing the desolvated ions from the electrospray (ES) chamber (which operates at atmospheric pressure) to the mass spectrometer (which operates at $10^{-6}$ to $10^{-4}$ Torr). The selection allows the introduction of ions without overwhelming the vacuum system and without sacrificing the sensitivity of the system, because the maximum amount of analyte is introduced into the vacuum system for mass analysis and detection.

Orthogonal ion sampling according to the present invention allows more efficient enrichment of the analyte by spraying the charged droplets past a sampling orifice while directing the solvent vapor and solvated droplets away in a direction such that they do not enter the vacuum system.

The noise level in an apparatus configured according to the present invention is reduced by as much as five fold over current systems, resulting in increased signal relative to noise hence, greater sensitivity. Performance is simplified and the system more robust because optimization of needle position, gas flow and voltages show less sensitivity to small changes. The simplified performance and reduced need for optimization also result in a system less dependent of flow rate and mobile phase conditions. The reduced need for optimization extends to changing mobile phase flow rates and proportions. This means that the system can be run under a variety of conditions without adjustment.

Another benefit of the invention taught herein is simplified waste removal owing to the fact that the spray can be aimed directly at a waste line and be easily removed from the system. Furthermore, the present invention provides the option of eliminating high voltage elements with no loss of sensitivity.

DETAILED DESCRIPTION OF THE INVENTION

Figure 1:
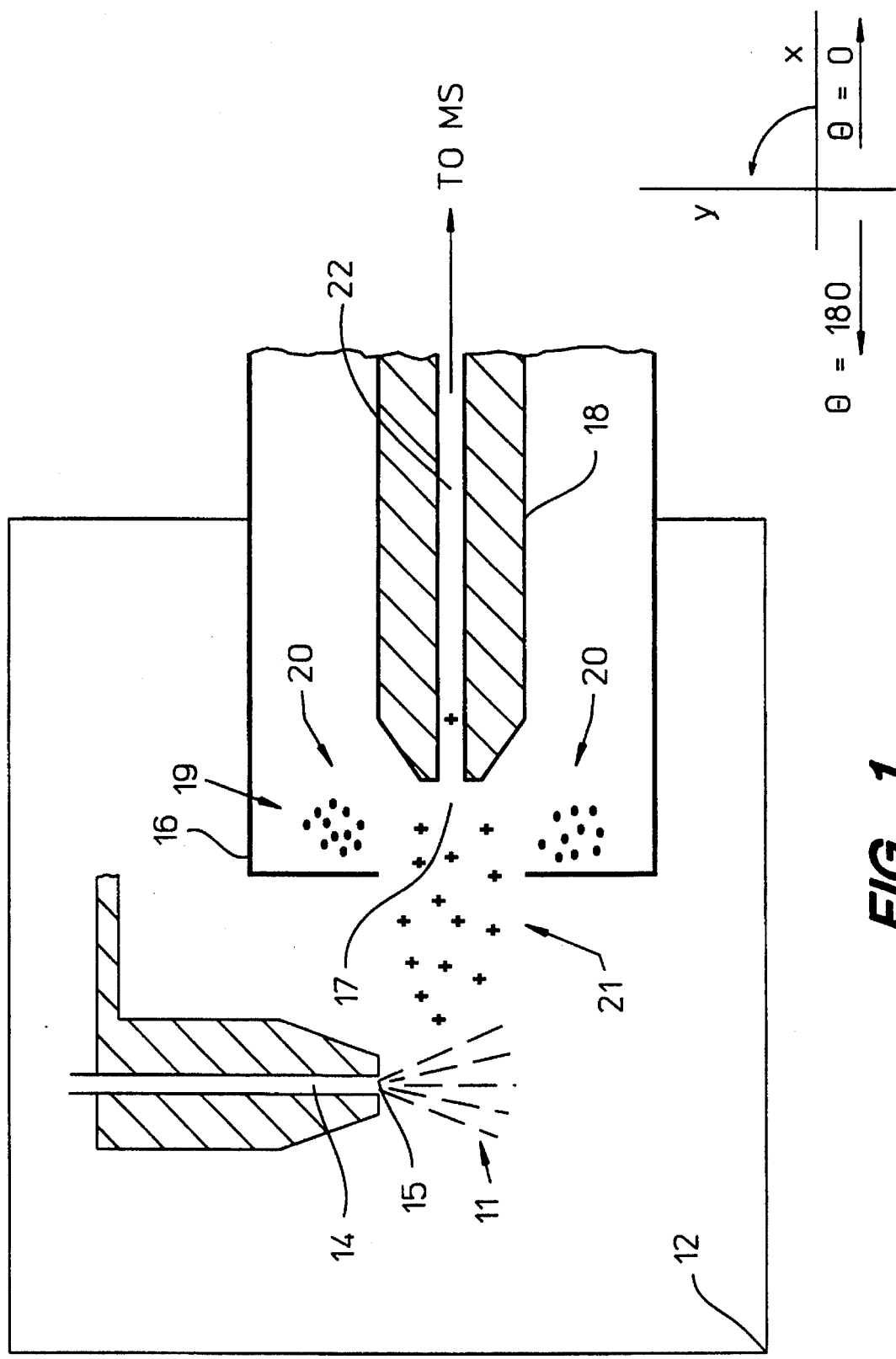
FIG. 1 is a representation of an apparatus according to the present invention.

FIG. 1 depicts an apparatus 10 configured according to the current invention. As in conventional sample introduction, a liquid sample is conducted through the nebulizer with a first passageway 14, exiting a second orifice or exit of the first passageway 15 under conditions which create a vapor of charged droplets or "electrospray" 11. The invention provides a rather different electrospray particle transport as compared with conventional electrospray. FIG. 1 depicts the transport of the electrospray droplets from the second orifice exit of the first passageway 15, through the distance to the entrance of the second passageway 17, and entering the second passageway 18 where the orientation angle $\ominus$ of the axis of the exiting electrospray 11 and the second passageway 22 is between 75 degrees and 105 degrees relative to each other. The angle may be greater than 105, in principle as great as 180; best results have been obtained at settings at or near 90 degrees. The charged droplets are electrostatically attracted laterally across the gap between the exit of the first passageway 15 into the opening of the second passageway 17. The electrostatic attraction is generated by attaching voltage sources to components of the apparatus. A first voltage source 16 is connected to a housing 19 which houses the second passageway 22. The housing is not necessarily an enclosure but may be in any shape that can act as a guide for the ions and can support fluid dynamics of a drying gas (see below discussion). A second voltage source 18 is connected to the second passageway 22. The first passageway 14 is generally kept at ground.

In the course of crossing the gap and approaching the entrance to the second passageway 22, especially after passing through an opening 21 in the housing 19 containing the second passageway 22, the electrospray is subjected to the cross flow of a gas 20—a condition that operates to remove solvent from the droplets, thereby leaving small charged droplets. The small droplets are amenable to analysis by operation of an analytic instrument capable of detecting and measuring mass and charge of particles such as a mass spectrometer (not shown). The second passageway exits into the mass spectrometer or equivalent instrument.

A standard electrospray system (HP 5989) with a pneumatic nebulizer provides the base structure. A spray box 12 of plexiglass or some other suitable material for preventing shock and containing noxious vapors replaces the standard spray chamber. Within the spray box 12, the nebulizer 14 may be arranged in a variety of configurations so long as the distance between the separate high voltage points is sufficient to prevent discharges. Additional surfaces at high voltage may be used to shape the electrical fields experienced by the spray. In the embodiment depicted in FIG. 1, the system includes a drying gas 20 to aid desolvation and prevent spray droplets 11 from entering the orifice of the second passageway 17 and the vacuum system (not shown).

An alternate embodiment could include a heated capillary as the second passageway 22 in an internal source off-axis geometry, such that the capillary is off-axis with respect to quadropole and detector components.

The configuration shown in FIG. 1 generally has the second voltage source 18 set typically at −4.5 kV, and the first voltage source 16 at −4 kV, and the first passageway 14 generally comprising a needle at ground. Gas, usually nitrogen at nominally 200 degree to 400 degree Centigrade and approximately 10 standard liter per minute, is typically used as a cross flow drying gas, although other gases can be used. The drying gas 20 flows across the aperture at approximately 90 degrees to the axis of the incoming charged molecules.

The term "passageway", as used in this application, means "ion guide" in any form whatever. It is possible that the passageway be of such short length relative to opening diameter that it may be called an orifice. Other ion guides, including capillaries, which are or may come to be used can operate in the invention. The configurations herein are not meant to be restrictive, and those skilled in the art will see possible configurations not specifically mentioned here but which are included in the teaching and claims of this invention.

EXAMPLES

A number of different configurations have proved possible. Examples of certain tested configurations follow.

Figure 2:
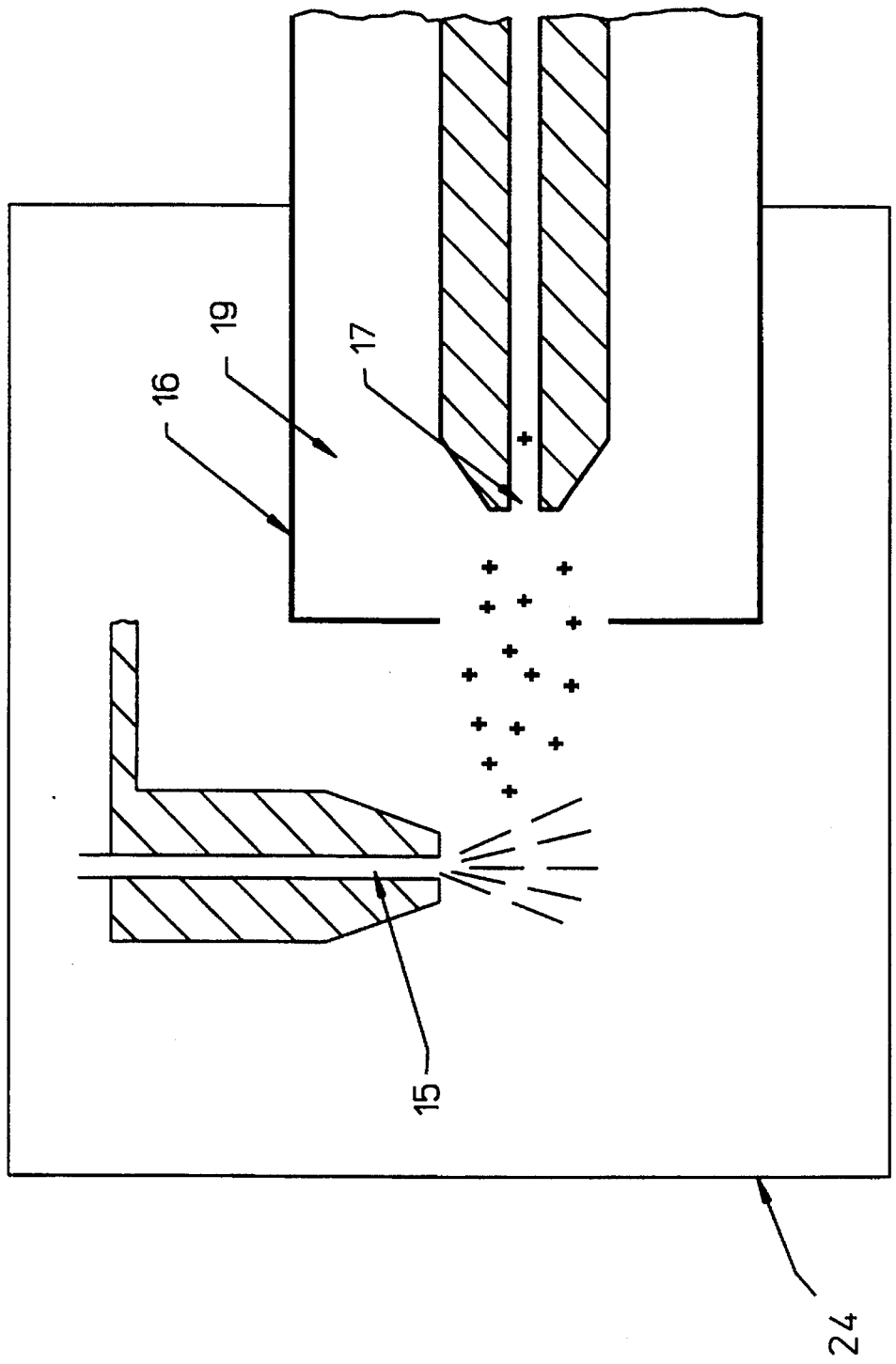
FIG. 2 is a representation of an alternate embodiment of an apparatus according to the present invention.

FIG. 2 shows a configuration of the invention in which a third voltage source, a plate 29 is positioned beside the exit of the first passageway 15 and distal to the side near to which the first voltage source 16 and opening to the second passageway cavity 17 are positioned. The plate 29 runs a positive voltage relative to the first voltage source 16. Experiments show the charged droplet electrospray "sees" a mean voltage between the plate 29 and the charged housing 19. Results suggest that the repeller effect may be captured and ion collection yield increased by careful sculpting of both the electric field and the gas flow patterns.

Figure 3:
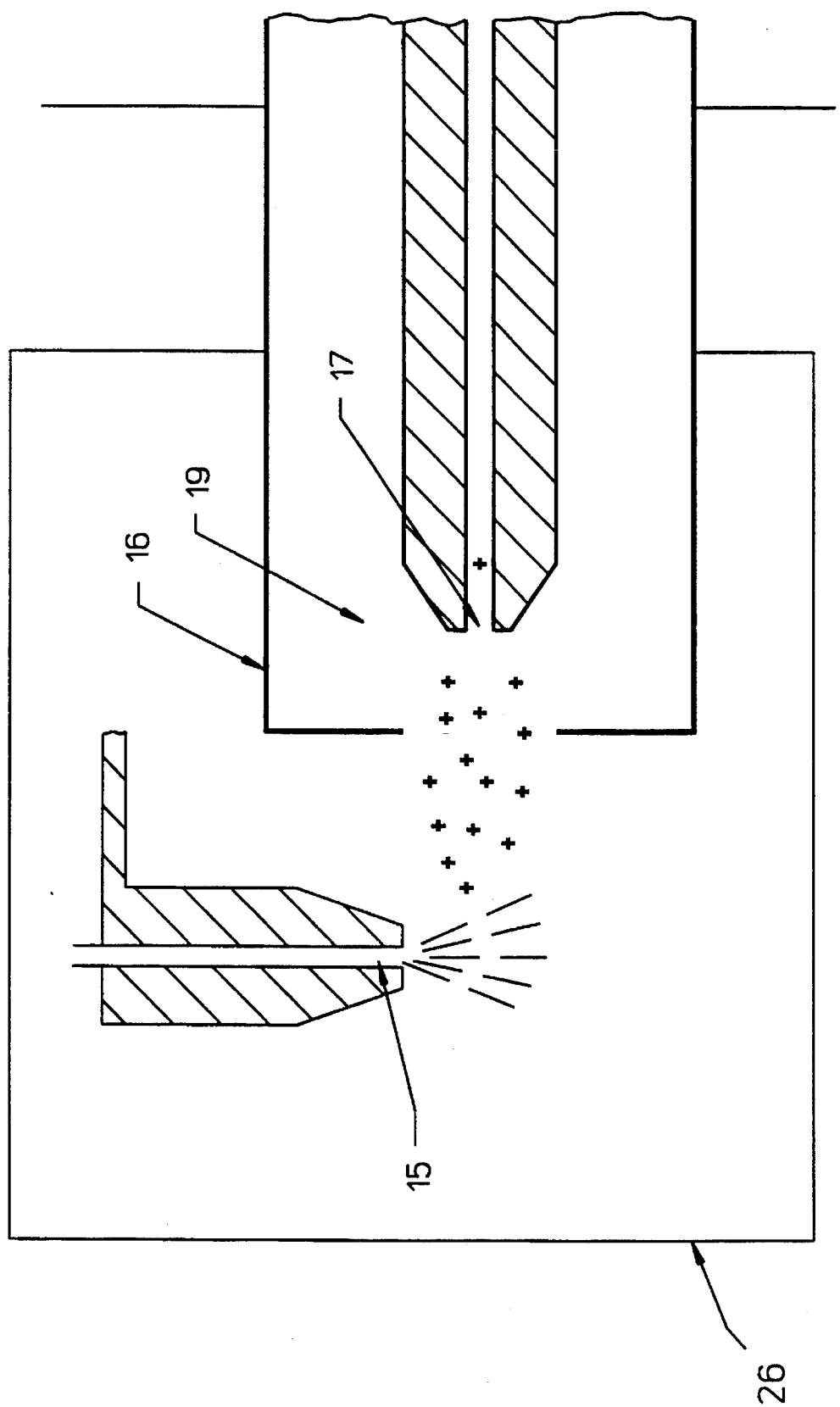
FIG. 3 is a representation of an alternate embodiment of an apparatus according to the present invention.

FIG. 3 shows a two voltage source system as in FIG. 2 with the addition of a grounded spray chamber 26. The spray chamber 26 operates to contain the aerosol and route condensed vapor to waste.

Figure 4:
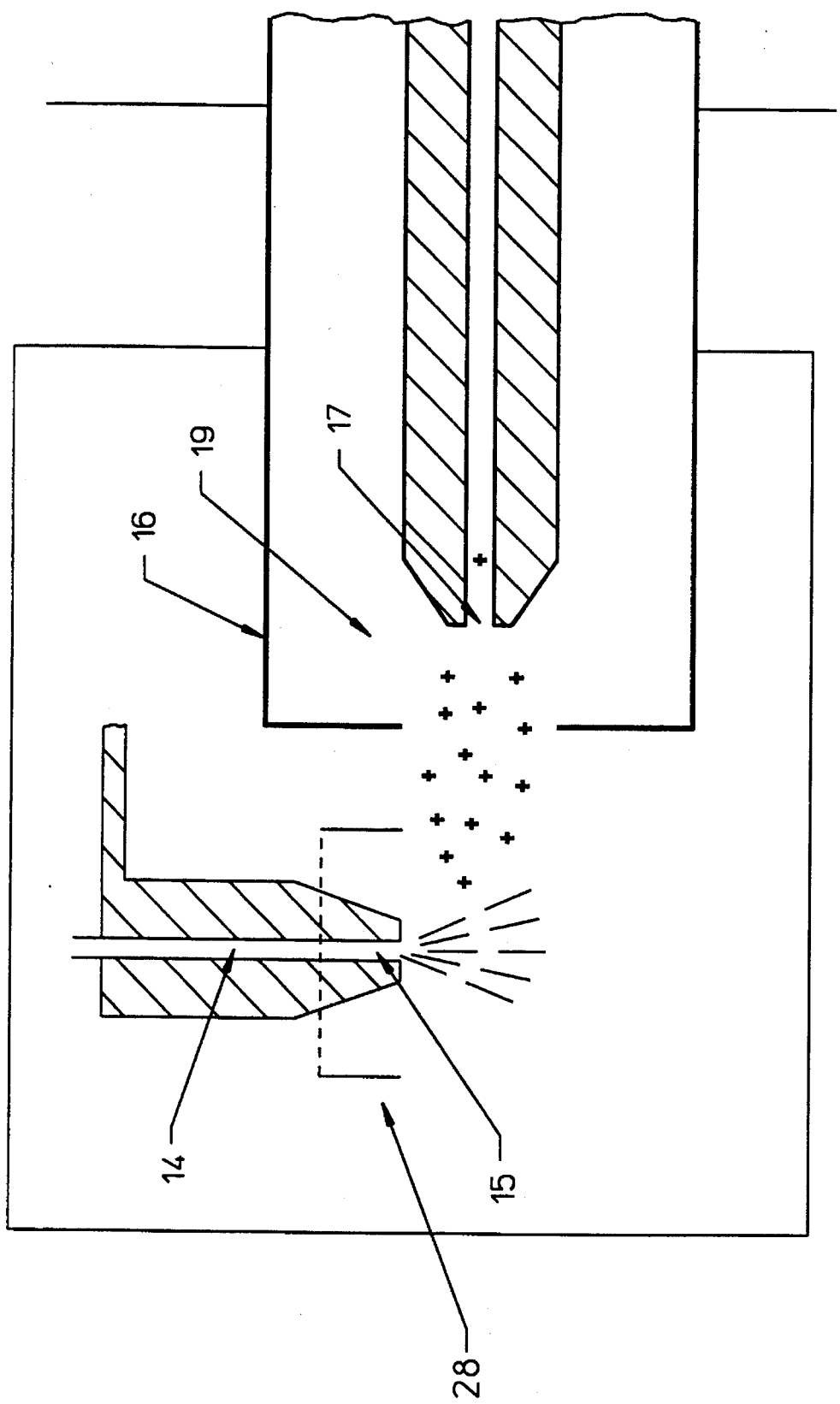
FIG. 4 is a representation of an alternate embodiment of an apparatus according to the present invention.

FIG. 4 shows the addition of a ring-shaped electrode 28 encircling the flow exiting from the needle or first passageway 14 at ground, with all of the elements configured as in FIG. 3. The ring-shaped electrode 28 induces a charge in the droplets by virtue of the potential difference in charge between the droplets and the ring-shaped electrode 28. Other potentials in the system can be used to direct the sampling of ions.

What is claimed is:

1. An apparatus for converting a solute sampled into ionized molecules, comprising:

a first passageway having a center axis, an orifice for accepting a solute sample and an exit for discharging the sample from the passageway in the form of an electrospray containing charged molecules;

an electrically conductive housing connected to a first voltage source and having an opening arranged adjacent to the first passageway exit; and a second passageway arranged within the housing adjacent to the opening and connected to a second voltage source, the second passageway having a center axis, an orifice for receiving charged molecules attracted from the electrospray and an exit, wherein the center axis of the second passageway is arranged in transverse relation to the center axis of the first passageway such that charged molecules in the electrospray move laterally through the opening in the housing and thereafter pass into the second passageway under the influence of electrostatic attraction forces generated by the first and second voltage sources.

2. The apparatus of claim 1 wherein an angle formed between the center axis of the first passageway and the center axis of the second passageway is greater than 75 degrees and less than or equal to 180 degrees.

3. The apparatus of claim 2 further comprising means for directing a stream of a drying gas in front of the orifice of the second passageway such that molecules passing through the opening in the housing encounter the stream of drying gas before entering the second passageway.

4. The apparatus of claim 3 wherein the first and second voltage sources provide a voltage difference, whereby the difference urges the charged molecules through the opening in the housing, across the stream of drying gas, and into the second passageway orifice.

5. The apparatus of claim 4 further comprising a third voltage source arranged adjacent to the exit of the first passageway, wherein the electrospray discharged from the first passageway is interposed between the third voltage source and the housing.

6. The apparatus of claim 3 wherein the first passageway comprises a needle and the second passageway comprises a capillary.

7. The apparatus of claim 6 wherein the second passageway is heated.

8. The apparatus of claim 3 wherein the second passageway comprises an orifice.

9. The apparatus of claim 1 further comprising an analytical apparatus in fluid communication with the second passageway exit, wherein the housing is interposed between the first passageway and the analytical apparatus.

10. The apparatus of claim 9 wherein the analytical apparatus is capable of detecting and measuring the mass and charge of molecules which have been communicated from the second passageway exit into the analytical apparatus.

11. The apparatus of claim 10 wherein the analytical apparatus comprises a mass spectrometer.

12. The apparatus of claim 11 further comprising means for directing a stream of a drying gas in front of the second passageway orifice such that molecules passing through the opening in the housing encounter the stream of drying gas before entering the second passageway.

13. The apparatus of claim 12 wherein the first and second voltage sources provide a voltage difference, whereby the difference urges the charged molecules through the opening in the housing, across the stream of drying gas, and into the second passageway orifice.

14. The apparatus of claim 13 further comprising a third voltage source arranged adjacent to the exit of the first passageway, wherein the electrospray discharged from the first passageway is interposed, between the third voltage source and the housing.

15. The apparatus of claim 12 wherein the first passageway comprises a needle and the second passageway comprises a capillary.

16. The apparatus of claim 15 wherein the second passageway is heated.

17. The apparatus of claim 12 wherein the second passageway comprises an orifice.

18. The apparatus of claim 4 further comprising a third voltage source arranged adjacent to the exit of the first passageway, wherein the third voltage source has an annular configuration and is positioned,such that the electrospray discharged from the first passageway is encircled by the third voltage source.

19. The apparatus of claim 13 further comprising a third voltage source arranged adjacent to the exit of the first passageway, wherein the third voltage source has an annular configuration and is positioned such that the electrospray discharged from the first passageway is encircled by the third voltage source.

* * * * *